United States Patent
Knebel et al.

(10) Patent No.: US 9,512,062 B2
(45) Date of Patent: Dec. 6, 2016

(54) METHOD FOR PRODUCING N-ISOPROPYL(METH)ACRYLAMIDE

(75) Inventors: Joachim Knebel, Alsbach-Haehnlein (DE); Wilhelm Karnbrock, Bensheim (DE); Volker Kerscher, Reinheim (DE)

(73) Assignee: EVONIK ROEHM GmbH, Darmstadt (DE)

( * ) Notice: Subject to any disclaimer, the term of this patent is extended or adjusted under 35 U.S.C. 154(b) by 94 days.

(21) Appl. No.: 13/119,244

(22) PCT Filed: Nov. 19, 2009

(86) PCT No.: PCT/EP2009/065435
§ 371 (c)(1),
(2), (4) Date: Mar. 16, 2011

(87) PCT Pub. No.: WO2010/072480
PCT Pub. Date: Jul. 1, 2010

(65) Prior Publication Data
US 2011/0218312 A1  Sep. 8, 2011

(30) Foreign Application Priority Data
Dec. 15, 2008 (DE) .......... 10 2008 054 612

(51) Int. Cl.
*C07C 213/02* (2006.01)
*C07C 231/02* (2006.01)
*C08F 220/56* (2006.01)
*C07C 233/09* (2006.01)

(52) U.S. Cl.
CPC .......... *C07C 231/02* (2013.01); *C08F 220/56* (2013.01); *C07C 233/09* (2013.01)

(58) Field of Classification Search
CPC .......... C07C 231/02; C07C 233/09
USPC .......... 526/303.1, 206; 564/144, 204
See application file for complete search history.

(56) References Cited

U.S. PATENT DOCUMENTS

| | | | |
|---|---|---|---|
| 4,288,592 A * | 9/1981 | Rauhut et al. | 544/159 |
| 4,859,796 A * | 8/1989 | Hurtel et al. | 564/204 |
| 6,927,290 B2 * | 8/2005 | Miki et al. | 540/607 |
| 8,445,723 B2 | 5/2013 | Morris | |
| 2003/0018152 A1 | 1/2003 | Angel et al. | |
| 2004/0024152 A1 | 2/2004 | Toyama et al. | |
| 2007/0238721 A1 | 10/2007 | Inagaki et al. | |
| 2010/0032284 A1 | 2/2010 | Krull et al. | |
| 2010/0048951 A1 * | 2/2010 | Morris | 564/144 |

FOREIGN PATENT DOCUMENTS

| | | |
|---|---|---|
| DE | 3412650 A1 * | 10/1985 |
| DE | 10 2006 047 617 | 4/2008 |
| JP | 50-59320 | 5/1975 |
| JP | 62-138460 | 6/1987 |
| JP | 3-264549 | 11/1991 |
| JP | 2004-500467 | 1/2004 |
| JP | 2012-500273 | 1/2012 |
| KR | 10-2011-0044236 | 4/2011 |
| RU | 2 137 740 C1 | 9/1999 |
| RU | 2011 105 303 A | 9/2012 |
| TW | 200604187 A | 2/2006 |
| WO | WO 96/41786 A1 | 12/1996 |
| WO | WO 02/10318 | 2/2002 |
| WO | WO 2010/021956 A2 | 2/2010 |

OTHER PUBLICATIONS

Hong, W, et al., "Identification of Aliphatic Amines From Rates of Cinnamoylation", J. Pharm. Sci, vol. 57, No. 10, pp. 1789-1790 (Oct. 1968) XP-002581558.
International Search Report Issued Jun. 2, 2010 in PCT/EP09/065435 filed Nov. 19, 2009.
Combined Taiwanese Office Action and Search Report issued Jul. 7, 2014 in Patent Application No. 098142285 (with English language translation).
Office Action issued Jul. 31, 2014 in Russian Patent Application No. 2011129251/04(043176) (with English language translation).
Office Action issued Nov. 11, 2013 in JP Patent Application No. 2011-541268.
Office Action issued Aug. 26, 2013 in Russian Patent Application No. 2011 129 251 (English Translation).
Office Action dated May 2, 2016, mailed in Korean Patent Application No. 10-2011-7010969, filed on Feb. 18, 2011, with English translation.

* cited by examiner

*Primary Examiner* — Ling Choi
*Assistant Examiner* — David L Miller
(74) *Attorney, Agent, or Firm* — Oblon, McClelland, Maier & Neustadt, L.L.P.

(57) ABSTRACT

A novel process is described which allows N-isopropyl (meth)acrylamide to be obtained in high purity and yield in a simple manner, by reacting methacrylic anhydride with isopropylamine, optionally in a solvent.

10 Claims, No Drawings

METHOD FOR PRODUCING N-ISOPROPYL(METH)ACRYLAMIDE

FIELD OF THE INVENTION

A process which allows N-isopropyl(meth)acrylamide to be obtained in high purity and yield in a simple manner, by reacting methacrylic anhydride with isopropylamine, optionally in a solvent, is described. The amide precipitates out during the reaction and can be isolated by filtration. A further product fraction can be precipitated out of the filtrate by neutralizing the methacrylic acid obtained as a by-product and thus be obtained additionally. Alternatively, the methacrylic acid can be separated by distillation from product dissolved therein.

Surprisingly, in contrast to textbook knowledge, the equimolar conversion of the reactants forms virtually no N-isopropylammonium methacrylate.

STATE OF THE ART

The Ritter reaction serves to prepare amides from nitriles and substrates which can form carbenium ions (for example tertiary or secondary alcohols in the presence of strong mineral acids). For instance, N-isopropyl(meth)acryl-amide can be prepared from (meth)acrylonitrile and isopropanol. DE 31 31 096 describes this process. For workup, the acid which functions as a solvent has to be neutralized, which generates large amounts of waste salt. On top of this, the product contains impurities, for example methacrylamide.

OBJECTIVE

Procedure of the Invention

The substituted (meth)acrylamide is obtained in a simple manner by initially charging the anhydride, optionally in a solvent, and metering in the amine, optionally with cooling.

After the end of the addition, a portion of the product formed has generally already crystallized out and can, optionally after cooling the product solution to complete the precipitation, be filtered off. To increase the yield, the (meth)acrylic acid present in the mother liquor can be neutralized, which leads to further precipitation of product. The product is formed virtually quantitatively. The substituted (meth)acrylamide obtained possesses a high purity, which is usually above 95%. For workup, the mother liquor can also be separated by distillation into N-isopropylmethacrylamide and methacrylic acid. Owing to the polymerization sensitivity of the monomers, it is appropriate to minimise the thermal stress in the course of this, for example by using a thin-layer evaporator. Purity and yield of the resulting monomers are higher than in the case of preparation by known processes such as the Ritter reaction or the use of carbonyl chloride as a raw material.

The Starting Materials

Anhydrides of the Unsaturated Carboxylic Acids

Useful anhydrides of the unsaturated carboxylic acids include acrylic anhydride, methacrylic anhydride or itaconic anhydride.

The methacrylic anhydride is traded, for example, by Evonik Röhm GmbH.

The Amines

The amines used may be primary amines and secondary amines. Useful primary amines include primary, optionally substituted aliphatic amines, for example methylamine, ethylamine, propylamine, butylamine, pentylamine, hexylamine, heptylamine, octylamine, dodecylamine, isopropylamine, isobutylamine and benzylamine, and also allylamine.

In addition, it is possible to use primary cycloaliphatic amines, for example cyclopropylamine, cyclobutylamine, cyclopentylamine and cyclohexylamine.

The primary aromatic amines used may be aniline, the isomeric aminotoluenes, individually or in mixtures, and the isomeric xylidines, individually or in mixtures. These compounds may optionally be substituted by one or more halogens.

Secondary aliphatic amines, for example dimethylamine, methylethylamine, diethylamine, dipropylamine, diisopropylamine, dibutylamine, dipentylamine, dihexylamine, diheptylamine and dioctylamine can likewise be used.

The Polymerization Inhibitors

Polymerization inhibitors are already known. For example 1,4-dihydroxybenzenes can be added for stabilization. However, it is also possible to use differently substituted dihydroxybenzenes. In general, such inhibitors can be represented by the general formula (I)

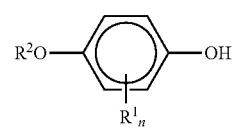

in which:

$R^1$ is hydrogen, a linear or branched alkyl radical having one to eight carbon atoms, halogen or aryl, preferably an alkyl radical having one to four carbon atoms, more preferably methyl, ethyl, n-propyl, isopropyl, n-butyl, isobutyl, sec-butyl, tert-butyl, Cl, F or Br;

n is an integer in the range from one to four, preferably one or two; and $R^2$ is hydrogen, a linear or branched alkyl radical having one to eight carbon atoms or aryl, preferably an alkyl radical having one to four carbon atoms, more preferably methyl, ethyl, n-propyl, isopropyl, n-butyl, isobutyl, sec-butyl or tert-butyl.

However, it is also possible to use compounds with 1,4-benzoquinone as the parent compound. These can be described by the formula (II)

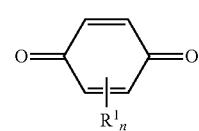

in which $R^1$ is a linear or branched alkyl radical having one to eight carbon atoms, halogen or aryl, preferably an alkyl radical having one to four carbon atoms, more preferably methyl, ethyl, n-propyl, isopropyl, n-butyl, isobutyl, sec-butyl, tert-butyl, Cl, F or Br; and n is an integer in the range from one to four, preferably one or two.

Equally, phenols of the general structure (III) are used.

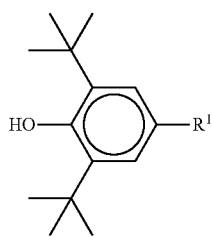
(III)

in which
$R^1$ is a linear or branched alkyl radical having one to eight carbon atoms, aryl or aralkyl, propionic esters with mono- to tetrahydric alcohols which may also contain heteroatoms such as S, O and N, preferably an alkyl radical having one to four carbon atoms, more preferably methyl, ethyl, n-propyl, isopropyl, n-butyl, isobutyl, sec-butyl, tert-butyl.

A further advantageous substance class is that of sterically hindered phenols based on triazine derivatives of the formula (IV):

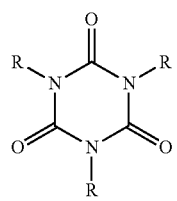
(IV)

where R=compound of the formula (V)

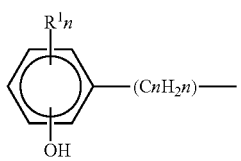
(V)

in which
$R^1 = C_nH_{2n+1}$
where n=1 or 2.

A further group of known inhibitors is that of amines, especially sterically hindered amines.

These include especially phenylenediamines which can be represented by formula (VI)

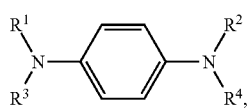
(VI)

in which $R^1$, $R^2$, $R^3$ and $R^4$ are each independently hydrogen and alkyl, aryl, alkaryl, aralkyl radicals having in each case up to 40 and preferably up to 20 carbon atoms, where preferably at least one of the $R^1$, $R^2$, $R^3$ and $R^4$ radicals is hydrogen.

Illustrative p-phenylenediamines include p-phenylenediamine in which the $R^1$, $R^2$, $R^3$ and $R^4$ radicals are each hydrogen; N-phenyl-N'-alkyl-p-phenylenediamines, for example N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-n-butyl-p-phenylenediamine, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine; N-phenyl-N',N'-dialkyl-p-phenylenediamines, for example N-phenyl-N',N'-dimethyl-p-phenylenediamine, N-phenyl-N',N'-diethyl-p-phenylenediamine, N-phenyl-N',N'-di-n-butyl-p-phenylenediamine, N-phenyl-N',N'-di-sec-butyl-p-phenylenediamine, N-phenyl-N'-methyl-N'-ethyl-p-phenylenediamine; N,N-dialkyl-p-phenylenediamines, for example N,N-dimethyl-p-phenylenediamine and N,N'-diethyl-p-phenylenediamine; N,N'-dialkyl-p-phenylenediamines, for example N,N'-diisopropyl-p-phenylenediamine, N,N'-diisobutyl-p-phenylenediamine; N,N'-diarylphenylenediamines, for example N,N'-diphenyl-p-phenylenediamine; N,N,N'-trialkyl-p-phenylenediamines, for example N,N,N'-trimethyl-p-phenylenediamine, N,N,N'-triethyl-p-phenylenediamine.

In addition, phenazine dyes constitute a further preferred group. These include especially induline and nigrosine. Nigrosine forms as a result of heating of nitrobenzene, aniline and aniline in hydrochloric acid solution with metallic iron and $FeCl_3$. Preference is given here to alcohol-soluble aniline dyes which may include, for example, 5 benzene rings, such as dianilido-N,N-diphenylphenosafranin. These substances are widely known and can be obtained commercially.

The compounds 1,4-dihydroxybenzene, 4-methoxyphenol, 2,5-dichloro-3,6-dihydroxy-1,4-benzoquinone, 1,3,5-trimethyl-2,4,6-tris-(3,5-di-tert-butyl-4-hydroxybenzyl)benzene, 2,6-di-tert-butyl-4-methylphenol, 2,4-dimethyl-6-tert-butylphenol, 2,2-bis[3,5-bis(1,1-dimethylethyl)-4-hydroxyphenyl-1-oxopropoxymethyl]1,3-propanediylesters, 2,2'-thiodiethyl bis[3-(3,5-di-tert-butyl-4-hydroxyphenyl)]propionate, octadecyl 3-(3,5-di-tert-butyl-4-hydroxyphenyl)propionate, 3,5-bis(1,1-dimethylethyl-2,2-methylenebis(4-methyl-6-tert-butyl) phenol), tris(4-tert-butyl-3-hydroxy-2,6-dimethylbenzyl)-s-triazine-2,4,6-(1H,3H,5H)trione, tris(3,5-di-tert-butyl-4-hydroxy)-s-triazine-2,4,6-(1H,3H,5H)trione, tert-butyl-3,5-dihydroxybenzene or diphenyl-p-phenylenediamine (DPPD) and also 4-hydroxy-2,2,6,6,-tetramethylpiperidine 1-oxyl, are used particularly successfully, hydroquinone monomethyl ether (4-methoxyphenol) being very particularly appropriate in turn among these.

The inhibitors mentioned are commercially available.

As base stabilization for ethylenically unsaturated compounds, the compounds mentioned can be used alone or in a mixture of two or more compounds. When the compounds are phenolic compounds, the presence of oxygen in the reaction mixture is required in order to ensure sufficient efficacy against polymerization. The use of air as an oxygen source is particularly preferred.

The Solvent

The solvents used may be all inert organic solvents, for example aliphatic hydrocarbons such as hexane, heptane, octane, cyclohexane, or mixtures of aliphatic hydrocarbons, for example petroleum ether, ligroin, decalin or benzine.

In addition, it is possible to use aromatic solvents, for example benzene, toluene or the isomeric xylenes, and mixtures of aforementioned compounds.

In addition, oxygen-containing hydrocarbons are useful, for example diethylene glycol monomethyl ether, diethylene glycol monoethyl ether, triethylene glycol monomethyl ether, triethylene glycol monoethyl ether, diethylene glycol monobutyl ether, diethyl ether or methyl tert-butyl ether. Water is also a possible inert solvent, since it brings about only a low level of hydrolysis of the (meth)acrylic anhydride under the reaction conditions of amide preparation.

EXAMPLES

Example 1

Preparation of N-isopropylmethacrylamide

A 2 l five-neck round-bottomed flask with mechanical stirrer, dropping funnel, air inlet tube, internal temperature sensor and reflux condenser is initially charged with 463 g (3 mol) of methacrylic anhydride, 504 g (6 mol) of cyclohexane and, as an inhibitor, 0.077 g (120 ppm based on reactants) of 2,6-di(tert-butyl)-4-methylphenol, and 177 g (3 mol) of isopropylamine are metered in at a temperature below 20° C. within 1.25 h with stirring and introduction of a gentle airstream. In the course of this, crystals precipitate out. After the end of the addition, the suspension is cooled to 4° C. to 8° C., and stirred for another 2.5 h to complete the precipitation. Thereafter, it is filtered and the crystals are washed twice with 60 g each time of cyclohexane and dried under air. Yield 188 g (49%) of N-isopropylmethacrylamide, purity 97.8% (determined by gas chromatography).

To neutralize the methacrylic acid present, the mother liquor is admixed with 280 g of 30% sodium hydroxide solution, which forms two phases. The mixture is stirred at room temperature for 0.5 h, in the course of which crystalline solids precipitate out. To complete the precipitation, the suspension is stored at 5° C. for 12 h. Thereafter, it is filtered and the filter cake is dried under air.

Yield: 165 g (43% of theory) of N-isopropylmethacrylamide, purity 93.8% (determined by gas chromatography).

Example 2

Preparation of N-dodecylmethacrylamide

A 1 l five-neck round-bottomed flask with mechanical stirrer, dropping funnel, air inlet tube, internal temperature sensor and reflux condenser is initially charged with 300 g (1.95 mol) of methacrylic anhydride and, as an inhibitor, 0.06 g (120 ppm based on product) of 2,6-di(tert-butyl)-4-methylphenol and 0.03 g (60 ppm based on product) of hydroquinone monomethyl ether and 0.003 g (6 ppm based on product) of 4-hydroxy-2,2,6,6-tetramethylpiperidine 1-oxyl, and 361 g (1.95 mol) of molten (m.p. 25 . . . 28° C.) of N-dodecylamine are metered in at a temperature of 30 . . . 35° C. within 1.3 h with stirring and introduction of a gentle airstream. After the end of the addition, the liquid, slightly viscous mixture is stirred at 40 . . . 45° C. for a further 3 h and cooled to room temperature. To distil off the methacrylic acid, the reaction vessel is provided with a distillation apparatus and heated to bottom temperature 97° C. in an oil-pump vacuum (1 mbar) within 3 h, which gives 154 g of methacrylic acid (92% of theory). The distillation residue consists of 490 g of N-dodecylmethacrylamide (99% of theory) with a purity determined by gas chromatography of 98%.

Example 3

Preparation of N-isopropylmethacrylamide

A 1 l four-neck round-bottomed flask with mechanical stirrer, dropping funnel, internal temperature sensor and reflux condenser is initially charged with 300 g (1.95 mol) of methacrylic anhydride and, as an inhibitor, 0.06 g (120 ppm based on product) of 2,6-di(tert-butyl)-4-methylphenol and 0.03 g (60 ppm based on product) of hydroquinone monomethyl ether and 0.003 g (6 ppm based on product) of 4-hydroxy-2,2,6,6-tetramethylpiperidine 1-oxyl, and 115 g (1.95 mol) of isopropylamine are metered in at a temperature of max. 30° C. within 3 h with stirring. After the end of the addition, the liquid, slightly viscous mixture is stirred at 40° C. for a further 3 h and cooled to room temperature. The precipitated crystals are filtered off with suction and washed with 157 g of cyclohexane, which is combined with the mother liquor. As the first fraction, 114 g (46% of theory) of N-isopropylmethacrylamide with a melting point of 89° C. and a purity determined by gas chromatography of 99% are obtained. For workup of the mother liquor, it is fed to a DS 25 laboratory thin-film evaporator (from NGW, Wertheim) with attached Vigreux column (length 10 cm), and the cyclohexane and the methacrylic acid are drawn off at a heating jacket temperature of 130° C. and a pressure of 1 mbar. The distillation residue solidifies when cooled to RT and consists of 130 g of N-isopropylmethacrylamide (52% of theory) with a purity determined by gas chromatography of 97%.

Comparative Example 1

Preparation of N-isopropylmethacrylamide from Methacryloyl Chloride

A 1 l four-neck round-bottomed flask with mechanical stirrer, dropping funnel, internal temperature sensor and reflux condenser is initially charged with 500 g (1 mol) of 2N sodium hydroxide solution, 59 g (1 mol) of isopropylamine and, as an inhibitor, 0.1 g of 2,4-dimethyl-6-(tert-butyl) phenol, and 104 g (1 mol) of methacryloyl chloride are metered in at room temperature with stirring. After the end of the addition, the mixture is stirred for a further 1 h, another 10 g of sodium hydroxide are added and the mixture is stirred for a further 30 min. The precipitated crystals are filtered off with suction and dried under air. This gives 108 g (85% of theory) of N-isopropylmethacrylamide with a purity determined by gas chromatography of 90.7%. As a by-product, 9% of an addition product of methylacryloyl chloride onto N-isopropylmethacrylamide is present.

Comparative Example 2

Preparation of N-isopropylmethacrylamide from Methacryloyl Chloride

A 1 l four-neck round-bottomed flask with mechanical stirrer, dropping funnel, air inlet tube, internal temperature sensor and reflux condenser is initially charged with 300 ml of toluene and 118 g (2 mol) of isopropylamine and, as an inhibitor, 0.1 g of 2,6-di(tert-butyl)-4-methylphenol, and 104 g (1 mol) of methacryloyl chloride are metered in at max. 30° C. with stirring and introduction of air. The precipitated product is filtered off with suction and dried. This gives 65 g (51% of theory) of N-isopropylmethacrylamide with a purity determined by gas chromatography of 82.4%. As a by-product, 1.3% of an addition product of methacryloyl chloride onto N-isopropylmethacrylamide and 11% methacrylic anhydride are present.

Comparative Example 3

Preparation of N-isopropylmethacrylamide from Methacrylonitrile According to Ritter in 100% Sulphuric Acid A 2 l four-neck round-bottomed flask with mechanical stirrer, dropping funnel, air inlet tube, internal temperature sensor and reflux condenser is initially charged with 515 g (5.25 mol) of 100% sulphuric acid, and a mixture of 168 g (2.5 mol) of methacrylonitrile, 180 g (3 mol) of isopropanol and 0.18 g of 2,6-di(tert-butyl)-4-methylphenol was metered in with stirring and introduction of air within 2.5 h. The exothermic reaction is maintained by cooling in the range from 22 to 25° C. After the end of the addition, the reaction is allowed to continue at 30° C. for 1 h, then the reaction mixture is heated to 60° C. and kept at this temperature for 1 h. Thereafter, it is cooled to room temperature and 750 g of water are added with cooling within 70 min, in such a way that the temperature does not rise. The mixture is transferred to a 4 l flask and a further 925 g of water are added, in the course of which solids separate out. 50% sodium hydroxide solution (approx. 815 g) are used to neutralize the mixture (pH=7) at max. 30° C. within 120 min. The mixture is cooled to 18° C., then the precipitated product is filtered off with suction and washed four times with 320 ml each time of cold water. The resulting crystal slurry is pressed dry. This gives 1136 g of product which, as well as N-isopropylmethacrylamide, contains 42% water and 22% sodium sulphate. The N-isopropylmethacrylamide fraction has a purity determined by gas chromatography of 93.5% and contains 5.9% methacrylamide.

The inventive compounds can be used as monomers to prepare polymers and copolymers. In addition, the inventive monomers can be polymerized to polymers or copolymerized in mixtures which are used as gas hydrate formation inhibitors.

The invention claimed is:

1. A process for preparing an amide of (meth)acrylic anhydride, the process comprising:
   metering an amine, which is a primary or a secondary amine, into a mixture consisting of (meth)acrylic anhydride and a polymerization inhibitor at a maximum metering temperature of 35° C. so that the amine reacts with the anhydride in the presence of the polymerization inhibitor at a maximum reaction temperature of 45° C. to yield the amide and a mother liquor comprising (meth)acrylic anhydride; and
   removing the amide from the mother liquor.

2. The process according to claim 1, further comprising neutralizing the mother liquor after said removing to precipitate out further amide; and
   removing the further amide.

3. The process according to claim 1, further comprising distilling the mother liquor after said removing to remove (meth)acrylic acid and obtain a distillation residue comprising further amide; and
   removing the further amide.

4. The process according to claim 1, wherein the amine is a primary amine.

5. The process according to claim 1, wherein the amine is a secondary amine.

6. A process for preparing N-isopropylmethacrylamide, the process comprising:
   metering isopropylamine into a mixture consisting of methacrylic anhydride and a polymerization inhibitor at a maximum metering temperature of 30° C. so that methacrylic anhydride reacts with isopropylamine to yield N-isopropylmethacrylamide in the presence of the polymerization inhibitor at a maximum reaction temperature of 40° C.; and
   isolating N-isopropylmethacrylamide.

7. A method for preparing a polymer or copolymer, the method comprising:
   metering an amine, which is a primary or a secondary amine, into a mixture consisting of (meth)acrylic anhydride and a polymerization inhibitor at a maximum metering temperature of 35° C. so that the amine reacts with the anhydride in the presence of the polymerization inhibitor at a maximum reaction temperature of 45° C. to yield an amide and a mother liquor comprising (meth)acrylic anhydride; and
   removing the amide from the mother liquor
   polymerizing a monomer comprising the amide of (meth)acrylic anhydride to obtain the polymer or copolymer.

8. A process for preparing an amide of an unsaturated carboxylic acid, the process comprising:
   metering an amine, which is a primary or a secondary amine, into a mixture consisting of an anhydride of the unsaturated carboxylic acid, and a polymerization inhibitor at a maximum metering temperature of 30° C. so that the anhydride reacts with the amine in the presence of the polymerization inhibitor to form the amide and a mother liquor comprising the unsaturated carboxylic acid; and
   removing the amide from the mother liquor.

9. The process according to claim 8, wherein the anhydride of the unsaturated carboxylic acid is an anhydride of an unsaturated aliphatic carboxylic acid.

10. The process according to claim 9, wherein the anhydride of the unsaturated aliphatic carboxylic acid is selected from the group consisting of acrylic anhydride, methacrylic anhydride, and itaconic anhydride.

* * * * *